(12) United States Patent
Everett et al.

(10) Patent No.: US 6,385,358 B1
(45) Date of Patent: May 7, 2002

(54) BIREFRINGENCE INSENSITIVE OPTICAL COHERENCE DOMAIN REFLECTOMETRY SYSTEM

(75) Inventors: Matthew J. Everett, Livermore; Joseph G. Davis, Lafayette, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/479,674

(22) Filed: Jan. 7, 2000

Related U.S. Application Data

(63) Continuation-in-part of application No. 09/050,571, filed on Mar. 30, 1998, now Pat. No. 6,175,669.

(51) Int. Cl.[7] ............................. G02B 6/00; G01D 9/02
(52) U.S. Cl. ............................................................ 385/12
(58) Field of Search ................................ 356/345, 351, 356/357, 358, 359, 360, 317; 385/12, 13, 15, 24, 39, 47, 51

(56) References Cited

U.S. PATENT DOCUMENTS

| | | | |
|---|---|---|---|
| 5,139,494 A | 8/1992 | Freiberg | 606/3 |
| 5,202,745 A * | 4/1993 | Sorin et al. | 356/73.1 |
| 5,268,741 A | 12/1993 | Chou et al. | 356/351 |
| 5,321,501 A * | 6/1994 | Swanson et al. | 356/345 |
| 5,441,053 A | 8/1995 | Lodder et al. | 128/664 |
| 5,459,570 A * | 10/1995 | Swanson et al. | 356/345 |
| 5,465,147 A | 11/1995 | Swanson | 356/345 |
| 5,540,676 A | 7/1996 | Freiberg | 606/3 |
| 5,573,531 A | 11/1996 | Gregory | 606/14 |

FOREIGN PATENT DOCUMENTS

WO  WO 99/02095  7/1997

* cited by examiner

Primary Examiner—Akm E. Ullah
Assistant Examiner—Michelle R. Connelly-Cushwa
(74) Attorney, Agent, or Firm—Alan H. Thompson; Michael C. Staggs

(57) ABSTRACT

A birefringence insensitive fiber optic optical coherence domain reflectometry (OCDR) system is provided containing non-polarization maintaining (non-PM) fiber in the sample arm and the reference arm without suffering from signal degradation caused by birefringence. The use of non-PM fiber significantly reduces the cost of the OCDR system and provides a disposable or multiplexed section of the sample arm. The dispersion in the reference arm and sample arm of the OCDR system are matched to achieve high resolution imaging. This system is useful in medical applications or for non-medical in situ probes. The disposable section of non-PM fiber in the sample arm can be conveniently replaced when contaminated by a sample or a patient.

48 Claims, 3 Drawing Sheets

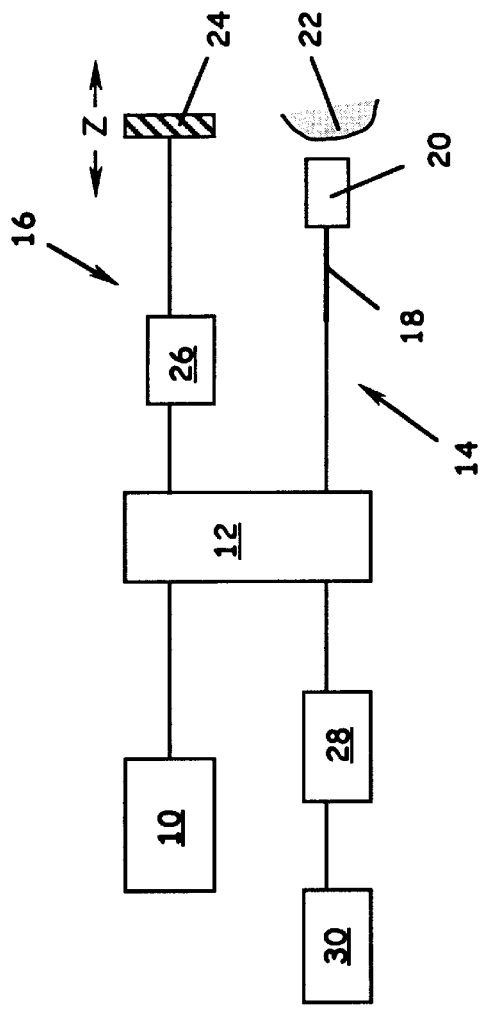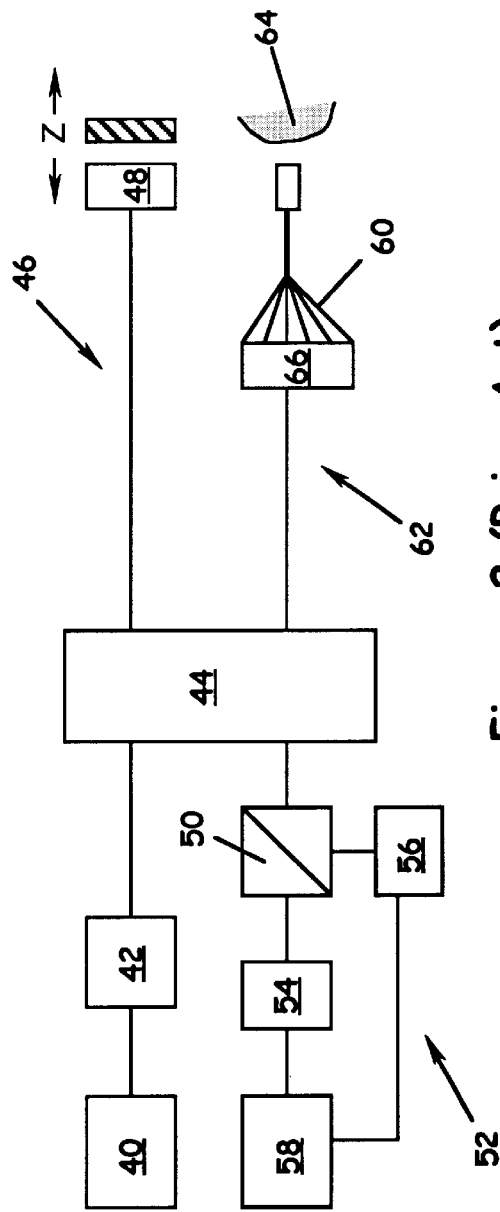

BIREFRINGENCE INSENSITIVE OPTICAL COHERENCE DOMAIN REFLECTOMETRY SYSTEM

This application is a continuation-in-part of U.S. patent application Ser. No. 09/050,571, filed Mar. 30, 1998 now U.S. Pat. No. 6,175,669.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates to a birefringence insensitive fiber optic optical coherence domain reflectometry (OCDR) system. In particular, the system is designed to provide a disposable section of non-polarization maintaining optical fiber in the sample arm while achieving high resolution by matching the dispersion between the sample arm and the reference arm.

2. Description of Related Art

Optical coherence domain reflectometry (OCDR) is a technique developed by Youngquist et al. in 1987 (Youngquist et al., "Optical Coherence-Domain Reflectometry: A New Optical Evaluation Technique", 1987, *Optics Letters* 12(3):158–160). A similar technique, optical coherence tomography (OCT), was developed and used for imaging with catheters by Swanson et al. in 1994 (See U.S. Pat. Nos. 5,321,501 and 5,459,570). OCDR and OCT have been applied to imaging and diagnoses of biological tissues, such as dental tissue (See U.S. Pat. No. 5,570,182 to Nathel et al.). OCT systems have been miniaturized to enable their use with guidewires. OCDR and guidewire systems are disclosed in WO 99/02113 (PCT/US98/14499) to Winston et al. and U.S. patent application Ser. No. 09/050,571 to Everett et al.

A diagram of a prior art OCDR scanning system is shown in FIG. 1. Light from a low coherence source 10 is input into a 2×2 fiber optic coupler 12, where the light is split and directed into a sample arm 14 and a reference arm 16. An optical fiber 18 in the sample arm 14 extends into a device 20 that scans an object 22. The reference arm 16 provides a variable optical delay. Light input into the reference arm 16 is reflected bade by a reference mirror 24. A piezoelectric modulator 26 may be included in the reference arm 16 with a fixed reference mirror 24, or the modulator 26 may be eliminated by scanning the mirror 24 in the Z-direction. The reflected reference beam from reference arm 16 and the scattered sample beam from sample arm 14 pass back through the coupler 12 to detector 28 (including processing electronics), which processes the signals by techniques that are known in the art to produce a backscatter profile or image on a display unit 30.

Standard fiber optic OCDR systems currently use non-polarization maintaining (non-PM.) fiber throughout, leading to loss of signal and to artifacts associated with mismatches between the polarization states of the light from the reference and sample arms (polarization fading). These mismatches are caused by birefringence in the sample and reference arms and the sample itself.

Several attempts have been made to eliminate this polarization fading through the use of polarization diversity receivers, where the light returning from the sample and reference arms is split into two orthogonal polarization modes each mode is detected by a separate detector. To minimize costs, such system would ideally have non-PM fiber in the sample arm. However all polarization insensitive systems developed to date with non-PM fiber in the sample arm have either suffered from dispersion caused by PM fiber in the reference arm, or variations in the polarization state of light returning from the reference arm, caused by changes in the birefringence of non-PM reference arm fiber.

Co-pending U.S. patent application Ser. No. 09/050,571 to Everett et al. describes a sensing system, shown in FIG. 2, in which the polarization of the light through the system is controlled by polarization maintaining (PM) fibers and optics. Linearly polarized light is introduced into the system either through use of a linearly polarized broadband light source 40 or by placing linear polarizer 42 directly after an unpolarized source 40. The linear polarization of the light is then maintained through the use of PM fibers and a PM fiber optic coupler 44, where the linear polarization is one of the two modes of the PM fiber and PM coupler 44. The polarization state of the light in the reference arm 46 is modified by either a waveplate or a faraday rotator 48 so as to be equally split between the two modes (orthogonal polarizations) of the PM fiber upon reflection. A polarization beam splitter 50 in the detector arm 52 splits the two polarization modes and directs them to two separate detectors 54,56 connected to the image processing and display unit 58.

In one embodiment shown in FIG. 2, the multiplexed optical fibers 60 in the sample arm 62 are polarization maintaining (PM). The sample arm 62 contains a multiplexer 66 for switching between the plurality of fibers 60, allowing sequential spatially distinct regions to be observed consecutively using the OCDR system. The fibers 60 can be oriented such that the light leaving the fibers is linearly polarized at an angle approximately 45° relative to the fast axis of birefringence of the sample 64. Alternatively, a quarter waveplate can be placed at the distal end of each fiber 60 to cause the light entering the sample 64 to be circularly polarized. In either case, the total light in all polarization states returning from the sample 64 is determined by summing the signal from the two detectors 54,56. In addition, processing and display unit 58 includes means for ratioing the output signals from detectors 54,56; the birefringence of the sample 64 is determined based on the arc tangent of the ratio of the signals from the two detectors 54,56.

In another embodiment described in U.S. patent application Ser. No. 09/050,571 to Everett et al., the optical fibers 60 in the sample arm 62 are not polarization maintaining (non-PM). In this case, the polarization beam splitter 50 ensures that the polarization state of the light from the reference arm 46 and the sample arm 62 is matched on each detector 54,56, thus eliminating the losses due to depolarization of the light. The light returning from the sample arm 62 is then measured by summing the signals from the two detectors 54,56.

It was found that the hybrid system described above containing non-PM fiber in the sample arm and PM fiber in the reference arm suffered from path length offsets between the two polarization modes, and reduced resolution caused by a difference in chromatic dispersion between the sample arm 62 non-PM fiber and the reference arm 46 PM fiber. Chromatic dispersion causes pulse broadening due to unequal speeds of different wavelength components of light in the reference arm fiber that are not matched by the sample arm non-PM fiber. The difference in the group velocity between the two polarization modes in the reference arm also lead to a path mismatch between the two polarization modes, which causes additional problems.

An alternate design for a fiber optic polarization insensitive OCDR system with non-PM fiber in the sample arm has previously been described (Kobayashi et al, "Polarization-Independent Interferometric Optical-Time-Domain Reflectometer", 1991, *J. Lightwave Tech.* 9(5):623–628). The reference arm in this system consists of all PM optical fiber, leading to loss of resolution due to mismatched dispersion between the sample and reference arms. The system also requires a specialized 50/50 coupler.

Another design of a polarization insensitive OCDR system is described by Sorin et al. in U.S. Pat. No. 5,202,745. In this design, a linear polarizer in the reference arm is adjusted to compensate for birefringence in the reference arm so as to equal signal powers on each detector in the detector arm in the absence of a signal from the test, or sample, arm. The problem with this approach is that the polarizer needs to be adjusted as the birefringence in the reference arm changes. As the birefringence in the non-PM reference arm fiber is strongly affected by temperature and stress, the system must be recalibrated with each use, and suffers from polarization drift during use.

Despite the problems with the systems described above, there is strong motivation to incorporate non-PM fiber into the sample arm, particularly to accommodate a disposable section at the end of the sample arm that interacts with the sample. For medical applications, the portion of the fiber optic interacting with the patient must be changed for hygienic reasons. The cost of PM fiber and PM fiber connectors makes disposable PM fiber based sensing arms impractical. Thus, a need exists to incorporate non-PM fiber into the sample arm while eliminating the dispersion effects that degrade image resolution.

The present invention addresses the above-mentioned problems and significantly improves on the system described in U.S. patent application Ser. No. 09/050,571 by providing a design for a less expensive, more robust, birefringence insensitive OCDR system that accommodates a disposable non-PM fiber in the sample arm, yet eliminates dispersion issues.

SUMMARY OF THE INVENTION

The object of the present invention is to provide a birefringence insensitive fiber optic optical coherence domain reflectometry (OCDR) system containing non-polarization maintaining (non-PM) fiber in the sample arm. Birefringence insensitive systems eliminate signal degradation caused by birefringence. Another object of the present invention is to minimize mismatches in dispersion between the sample and reference arms, while maintaining a disposable section of non-PM fiber in the sample arm. This is accomplished through the use of matching non-PM fiber in the reference arm. A further object of the invention is to provide a portable, robust OCDR system that can be used in medical applications or for non-medical in situ probes. A further object of the invention is to provide a means of incorporating a single mode fiber optical path modulator in the system for providing optical path scanning. A further object of the invention is to provide a means for more efficiently coupling of optical power to and from the sample arm.

In the present invention, the disposable portion of non-PM optical fiber in the sample arm is useful for incorporation into various clinical devices such as catheters, guidewires, and hand-held instruments or probes. The use of non-PM fiber significantly reduces the cost of these devices. Disposable sections of non-PM fiber can be incorporated into both the sample arm and the reference arm to permit convenient replacement of fibers used on patients or to rapidly configure OCDR systems with different path lengths.

Many OCDR systems, particularly in medical applications, require a portion of the sample arm that is either disposable or multiplexed. The use of polarization maintaining (PM) fiber throughout the OCDR system in conjunction with a polarization diversity receiver is beneficial from the standpoint of eliminating signal fading associated with birefringence. The use of non-PM fiber in the disposable or multiplexed portion of the sample arm is preferable due to its significantly reduced cost. However, the use of non-PM fiber in the sample arm with PM fiber in the reference arm causes the OCDR system to suffer loss of resolution due to mismatches in dispersion between the two arms.

These problems are overcome in the present invention by matching the dispersion in the sample arm (having a section of non-PM fiber) with dispersion in the reference arm in the OCDR system. It is an object of this invention to accomplish this dispersion matching using a section of non-PM fiber in the reference arm. Birefringence effects in this non-PM fiber are then eliminated using a faraday rotator between the non-PM fiber and reference miror. This faraday rotator rotates the polarization of the light so that light is returned through the fiber at 90° to its polarization state just prior to the faraday rotator, thus cancelling the effects of birefringence in the fiber. In one embodiment of this invention an additional faraday rotator, which rotates the polarization of light by approximately 45° upon double passing is placed between the PM and non-PM fiber in the reference arm. This faraday rotator causes the returning light from the reference arm, which was initially in a single polarization mode of the PM fiber, to be split between the two polarization modes. The polarization diversity receiver then consists of two or more detectors, which detect light in each of the two polarization modes of the fiber. In an alternative embodiment of the invention, essentially all or all fiber used in the reference arm and the sample arm is non-PM fiber. Once again, a polarization diversity receiver collects the light in each of two orthogonal polarization modes. This design is significantly less expensive, but suffers from polarization drift in the source and detector arm optical fibers, which are not double passed. This can be minimized by using optical fibers that are as short as possible.

In yet another embodiment, the detector arm and source arm of the system can be combined to form a more efficient system. In this case, use of coupler which couples more than 50% of the light from the source/detector arm to the sample arm and back can increase the sensitivity of the system. Use of a 90/10 coupler in this system would allow up to 81% of the light from the source to interact with the sample and return versus a maximum of 25% obtained with a 50/50 coupler if the source and detector are in separate arms. The combination source/detector arm contains a plurality of beamsplitters and detectors to collect the light.

The present invention is useful for medical applications, particularly in ophthalmology, dentistry, and cardiology, as it eliminates birefringence effects in both the tissue sample and fiber optics. Birefringence in biological tissues, such as the eye or dental tissue, leads to artifacts in images with conventional OCT systems. Artifacts and signal fading associated with birefringence in optical fibers is also a serious problem in clinical systems, particularly in catheter or guidewire based OCDR imaging systems. The catheter or guidewire in these systems must be replaced for each patient. The present invention provides the ability to incorporate non-PM optical fiber in those systems to significantly lower costs and facilitate the replacement of portions of the sample arm, while eliminating artifacts and signal losses due to polarization fading.

The present invention can also be used in non-medical applications where the fiber or probe in the sample arm becomes damaged or contaminated by the sample being imaged, and thus the fiber must be replaced repeatedly. The use of non-PM fiber in such systems is therefore advantageous and cost-effective. The invention can be used as a single point probe to examine defects in fiber optics, for example, or the sample arm can be scanned to form two-dimensional images or depth-resolved images. Other objects, features, and advantages of the present invention will become apparent from the following description and accompanying drawings.

DESCRIPTION OF THE DRAWINGS

The accompanying drawings, which are incorporated into and form part of this disclosure, illustrate embodiments of the invention and together with the description, serve to explain the principles of the invention.

FIG. 1 shows a prior art OCDR system.

FIG. 2 shows an OCDR guidewire optical sensing system with multiplexed sample arm using polarized light.

DETAILED DESCRIPTION OF THE INVENTION

The present invention is a birefringence insensitive fiber optic optical coherence domain reflectometry (OCDR) system that contains non-polarization maintaining (non-PM) optical fiber in the sample arm and the reference arm without suffering from signal degradation caused by birefringence. A section of non-PM fiber can be replaceable or multiplexed. The use of non-PM optical fiber significantly reduces the cost of the OCDR system. The invention provides a portable, robust OCDR system that can be used in medical applications or for non-medical in situ probes.

Most conventional designs for OCDR are birefringence sensitive, i.e., the systems suffer from signal fading and artifacts due to birefringence effects in the fiber in the sample arm and in the sample itself. Using polarization maintaining (PM) fiber throughout the OCDR system can solve these problems. However, if a portion of the sample arm is disposable or multiplexed, PM fiber is not practical due to the cost of PM fiber and connectors. (PM fiber has two principal orthogonal axes: a fast axis having the lower index of refraction and a slow axis having the higher index of refraction.)

Figure 3:
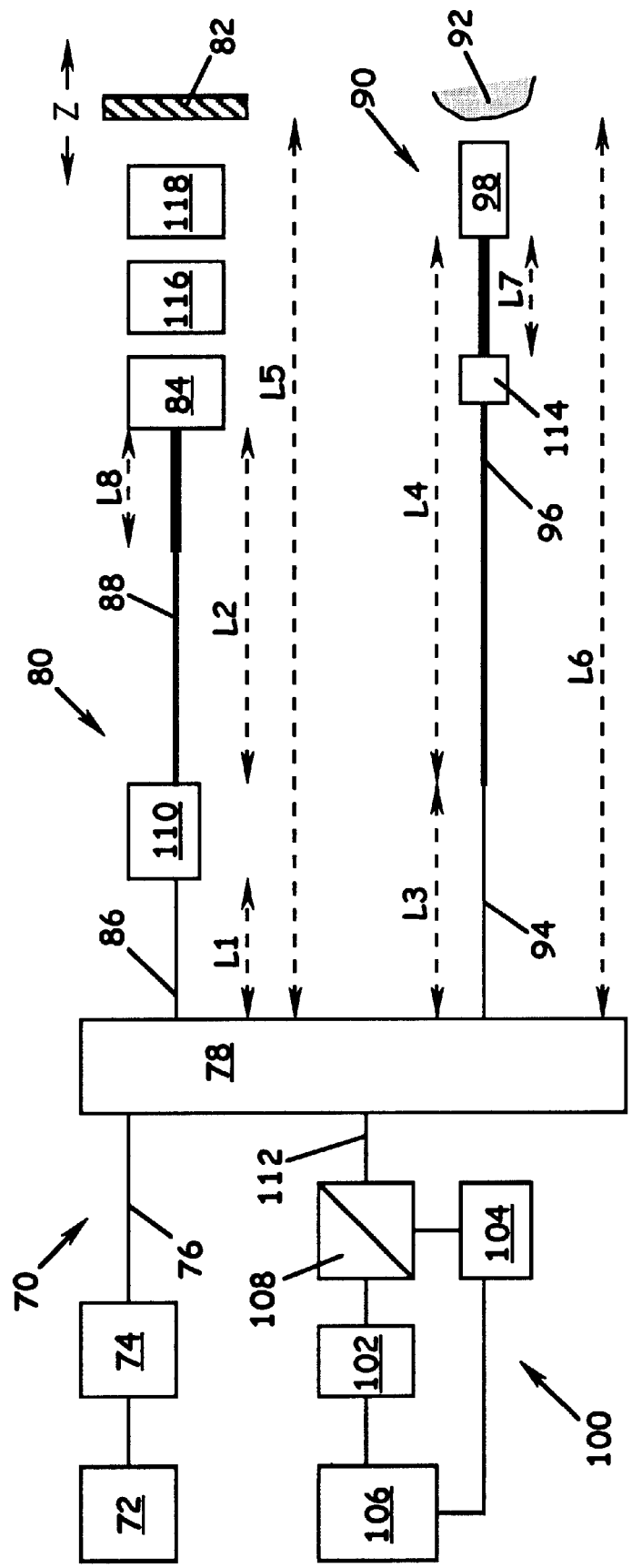
FIG. 3 shows an OCDR system according to the present invention.

FIG. 3 is a diagram of an OCDR system according to the present invention. The source arm 70 introduces linearly polarized light into the system either through a linearly polarized broadband light source 72 or by placing a linear polarizer 74 directly after an unpolarized source 72. The light source 72 (and polarizer 74) is coupled to an input PM fiber 76. The linear polarization of the light is maintained through the use of the PM fiber 76 and a 2×2 PM fiber optic coupler 78, where the linear polarization is one of the two modes (i.e., fast and slow axes) of the PM fiber 76 and PM coupler 78.

Output from the source 72 is split at the 2×2 fiber optic coupler 78 into two optical fiber outputs and directed through a sample arm 90 to a sample 92 and through a reference arm 80 to a reference mirror 82. Reflections from the mirror 82 and reflected or backscattered light from the sample 92 are recombined at the coupler 78 and propagated to the detector arm 100 (and to source arm 70). The detector arm 100 includes a plurality of detectors 102,104 (typically two) with associated processing electronics that produce a backscatter profile on an image processing and display unit 106 by methods known in the art. The system can be used as a single-point probe; additionally, the unit 106 may provide means for generating cross-sectional images of the sample.

Coherent interference creates a signal at the detectors 102,104 when the sample and reference reflections have traveled approximately the same optical group delay. The shorter the coherence length of the source, the more closely the sample and reference arm group delays must be matched for interference to occur. By imposing a changing optical delay in the reference arm 80 with a known velocity, either by scanning mirror 82 in the Z-direction or with a piezo-modulator (not shown) to vary the path length of the reference arm 80, the amplitudes and longitudinal positions of reflections from the sample 92 can be measured with high precision. A piezoelectric modulator can be alternatively or additionally placed in the sample arm 90 to increase the relative path variation between the reference arm 80 and the sample arm 90, i.e., to vary the path length of the reference arm with respect to the path length of the sample arm.

The polarization of the light through the OCDR system is controlled by PM optical fibers and optics. The polarized light entering the reference arm 80 travels through a length L1 of PM fiber 86 and a length L2 of non-PM fiber 88. The polarization state of the light from the PM fiber 86 is modified by a polarization optical element 110 that rotates the polarization by approximately 22.5° before entering the non-PM fiber 88, or 45° upon double passing through the reference arm 80. A suitable optical element 110 is a 22.5° faraday rotator. The light from the non-PM fiber 88 is modified by a rotator optical element 84 that rotates the polarization by 45° before reflecting off the mirror 82, or 90° upon double passing through the reference arm 80. A suitable optical element 84 is a 45° faraday rotator.

The polarization state of the light returning from the mirror 82 is modified (a second time) by the 45° faraday rotator 84, passes through the non-PM fiber 88, is modified (a second time) by the 22.5° faraday rotator 110, and passes through the PM fiber 86 to the PM coupler 78. The light passes from the coupler 78 into PM fiber 112 in the detector arm 100. Since the 45° faraday rotator 84 eliminates the birefringence effects (or changes in birefringence) in the non-PM fiber 88, the light entering the detector arm 100 from the reference arm 80 has a defined, or pre-determined, polarization state. The defined polarization state is independent of, or unaffected by, changes in birefringence in the non-PM fiber 88 in the reference arm 80. The 22.5° faraday rotator 110 causes the light to be split equally into the two polarization modes of the PM fiber as it rotates the polarization of the light by a total of 45°. While a total rotation of 45° is optimal, any amount of total rotation other than 0° or 90° by faraday rotator 110 will couple light into the second orthogonal polarization mode of the fiber. An optical element 108 in the detector arm 100, such as a polarization beam splitter, splits the light from fiber 112 into the two orthogonal polarization modes and directs them to the detectors 102,104 connected to the image processing and display unit 106. Preferably, the polarization beam splitter 108 splits the light equally between the two detectors 102,104.

The polarized light entering the sample arm 90 travels through a length L3 of PM fiber 94, followed by a length L4 of non-PM fiber 96 to the sample 92. The PM fiber 94 and non-PM fiber 96 are spliced together or connected by other conventional means. The light reflected or scattered from the sample 92 passes back through the non-PM fiber 96 and PM fiber 94 to the PM coupler 78 and into PM fiber 112 in the detector arm 100. The polarization beam splitter 108 in the detector arm 100 splits the polarization state of the light from the fiber 112 into two modes (orthogonal polarizations) and directs them to the detectors 102,104 connected to the image processing and display unit 106.

The total light in all polarization states returning from the sample 92 is determined by summing the envelope of the heterodyned signals from the two detectors 102,104. If there were mismatched dispersion between the reference arm and sample arm, the two signals from the detectors would be broadened, decreasing the resolution of the system. Since the dispersion is matched in the reference arm and sample arm in the present invention, the signals are not broadened and thus high image resolution is achieved.

The total optical path length L5 of the reference arm 80 (i.e., from coupler 78 to mirror 82) is substantially equal to the total optical path length L6 of the sample arm 90 (i.e., from coupler 78 to sample 92). Any combination of PM and non-PM fibers can be used as long as path lengths L5 and L6 are substantially equal. The lengths L1 and L3 of the PM fibers 86,94 are preferably of approximately equal length to match wavelength and polarization dispersion between the reference arm 80 and sample arm 90. As the path lengths L5 and L6 of the reference arm 80 and sample arm 90 are matched, the lengths L2 and L4 of the non-PM fibers 88,96 in the reference arm 80 and sample arm 90 are also of approximately equal length. The fiber and path lengths L1-L6 can be varied for different designs and applications of the OCDR system. In addition, a piezoelectric transducer (PZT) may be used to vary the path length in either or both the reference arm (L5) and the sample arm (L6) by wrapping the optical fiber around the transducer.

A distal portion or section L7 of the length L4 of the non-PM fiber 96 that interacts with the sample 92 may be a replaceable or disposable section. This replaceable section L7 may be connected to the remainder of the non-PM fiber 96 by a connector 114. This approach is preferred for medical device applications, where the section of fiber interacting with a patient (or incorporated into a device such as a guidewire or probe) must be detachable and replaceable for hygienic reasons. The detached section may be disposable, or sterilized and reused in some cases.

A corresponding section L8 (of the length L2) of the non-PM fiber 88 in the reference arm 80 that matches the length of the replaceable section L7 of non-PM fiber 96 in the sample arm 90 can also be replaceable. This approach allows the length and dispersion characteristics of the disposable fiber in the sample arm 90 to be matched by a fiber in the reference arm 80 of appropriate length and dispersion characteristics. For OCDR systems where dispersion is critical, it may be necessary to use the same fiber lot number for the replaceable fibers in the sample arm and reference arm. In some cases, it may be appropriate or convenient for the entire length L4 (and optionally L2) of the non-PM fiber in the sample arm 90 (and in reference arm 80) to be replaceable or disposable, not just a distal section.

A device 98 may be attached to or placed at the distal end of the non-PM fiber 96 in the sample arm to better direct or focus the light on the sample 92 (e.g., on or in a patient) and to enhance light collection. The device 98 may include one or more optical devices, e.g., graded index (GRIN) lens, bulk optic lens, mirror, prism, or a wave plate. Alternatively, a distal section of optic fiber may be incorporated into a device 98 such as a catheter, guidewire, probe, or other handheld instrument or handpiece. By using a distal section of non-PM fiber incorporated into the device 98, this section of fiber can be conveniently and inexpensively disposed of and replaced. The device 98 may contain means to transversely scan light across the sample, which enables generation of cross-sectional images of the sample.

In another embodiment of the OCDR system, the sample arm 90 contains a multiplexer or optical switch (such as element 66 shown in FIG. 2) for switching between a plurality of non-PM fibers, allowing sequential spatially distinct regions to be sampled consecutively using the OCDR system. In addition, a dispersion compensator 116 may be placed between the rotator element 84 and the reference mirror 82 to compensate for additional differences in dispersion between the sample and reference arms. The reference arm 80 can also include an attenuator 118 between the rotator element 84 and the reference mirror 82 to reduce the power returning to the detectors 102,104 from the reference arm 80. If the optical power returning from the reference arm 80 is too large, then the sensitivity of the system may be reduced due to either saturation or optical source noise.

Figure 4:
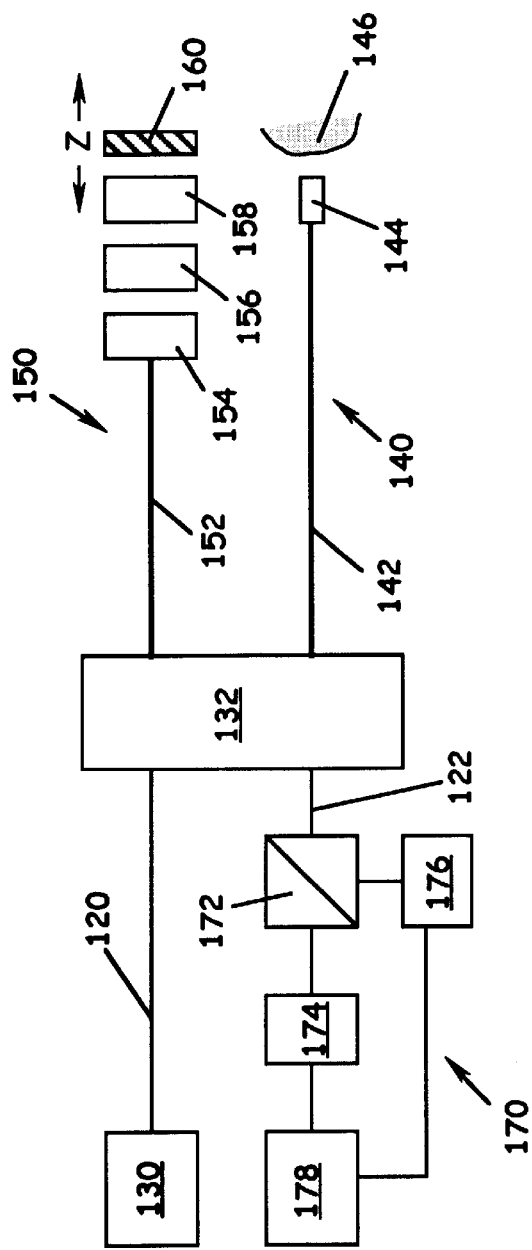
FIG. 4 shows an alternative embodiment of the OCDR system according to the present invention.

FIG. 4 shows an alternative embodiment of a birefringence insensitive OCDR system according to the present invention using all or essentially all non-PM fiber. Linearly polarized light from a source 130 passes through non-PM fiber 120 and enters a non-PM coupler 132, where the light is split and directed to the sample arm 140 and the reference arm 150. The light in the reference arm 150 passes through non-PM fiber 152 followed by a 45° per pass faraday rotator 154 for a total of 90° rotation after reflection from the reference mirror 160. The faraday rotator 154 cancels the birefringence from the non-PM fiber 152, leading to linearly polarized light returning from the reference arm 150 to the coupler 132. The coupler 132 may be a fiber optic non-PM coupler (e.g., 2×2) or may be replaced by a bulk optic beamsplitter. The reference arm 150 may include a dispersion compensator 156 and/or an attenuator 158 positioned after the non-PM fiber 152.

Light entering the sample arm 140 passes through non-PM fiber 142 (including an optional disposable section) and optionally through a device 144 to the sample 146. The device 144 is such as described for FIG. 3. The reflected light returning from the reference arm 150 and the sample arm 140 passes through the coupler 132 and fiber 122 into the detector arm 170. As in FIG. 3, the path lengths of the sample arm 140 and the reference arm 150 are approximately equal. The lengths of non-PM fibers 120,122 should be minimized to minimize bireftingence effects. If the coupler 132 is replaced by a bulk optic beamsplitter, then the non-PM fibers 120,122 can be eliminated.

The detector arm 170 includes a polarization optic 172 aligned at 45° relative to the linearly polarized light returning from the reference arm 150. The light entering the detector arm 170 from the reference arm 150 has a defined, or preselected, polarization state. The polarization optic 172, such as a polarization beam splitter, splits the light from the reference arm 150 equally into the two orthogonal modes, where each mode is detected by one of a plurality of detectors 174,176 (typically two, as shown). The detectors are connected to an image processing and display unit 178 to process the data and generate images using methods known in the art.

This alternative approach shown in FIG. 4 is inexpensive, but has the drawback that if the coupler 132 is a fiber optic (2×2) coupler, the birefringence of the non-PM fiber in the coupler 132 and in the fiber 122 (between the coupler 132 and the polarization optic 172 in the detector arm 170) may drift slightly over time, causing the relative amplitude of the light in the two polarization modes to drift. To optimize equal splitting of the light from the reference arm 150 between the two detectors 174,176, the optical fiber 120,122 in the source arm and/or the detector arm 170 can be bent until the polarization state of the light is split equally between the two polarization modes. The bent fiber can be held in the desired position by a fixture that permits subsequent adjustment or repositioning. The use of a bulk optic beamsplitter in place of the coupler 132 also eliminates this problem.

Figure 5:
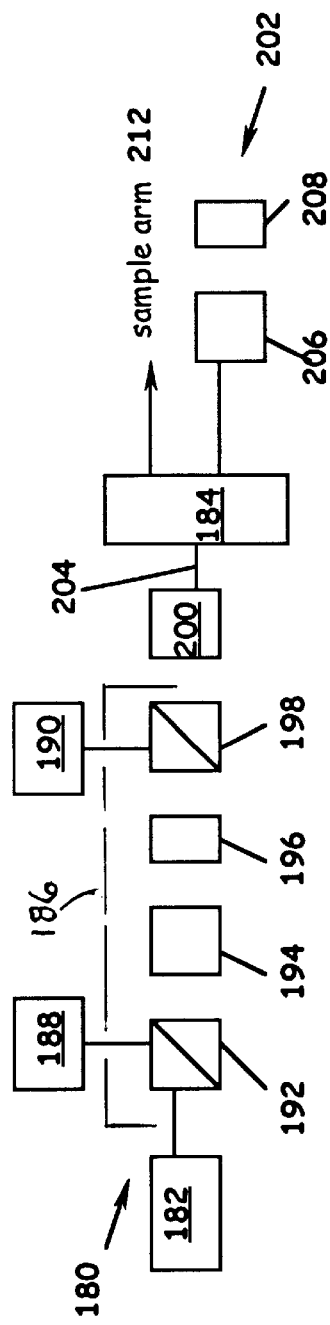
FIG. 5 shows an alternative embodiment of the OCDR system according to the present invention in which the source arm and detector arm are integrated.

FIG. 5 shows another alternative embodiment that uses all or essentially all non-PM fiber throughout the system. The detector arm is incorporated into the source arm 180 through the use of a specialized optical isolator 186, which comprises multiple optical elements and directs light from an unpolarized source 182 to a coupler 184, while redirecting light returning from the coupler 184. The optical isolator 186 collects all the light returning to the source arm 180 and redirects it, splitting the orthogonal polarization states between a plurality of detectors, typically two detectors 188,190 as shown.

A polarizer 192 polarizes the light from the source 182. This polarized light then passes through a 45° faraday rotator 194, optionally followed by a half wave-plate 196, to a second polarizer 198, which is orientated so as to pass all the light making it through polarizer 192. The half waveplate 196 can be used between the polarizers 192,198 so as to rotate the linearly polarized light and allow more freedom in the orientation of polarizer 198. A 22.5° faraday rotator 200 is placed immediately after polarizer 198. Light leaving the source arm 180 is linearly polarized after leaving polarizer 198. The portion of this light that goes to the reference arm 202 (and returns) passes through the 22.5° faraday rotator 200, followed by a section of non-PM fiber 204 and a2×2 fiber optic coupler 184, to a 45° faraday rotator 206 positioned at the end of the optical fiber in the reference arm 202. Upon reflection from reference mirror 208, light passes back through the 45° faraday rotator 206, the non-PM fiber 204 and 22.5° faraday rotator 200, resulting in light polarized 45° relative to polarizer 198. Half of this light is then deflected by polarizer 198 to detector 190. The other half of the light, in the orthogonal polarization, passes through polarizer 198 and is deflected by polarizer 192 into detector 188. The 22.5° faraday rotator 200 is used to split the light from the reference arm 202 between the two polarization states, and the 45° faraday rotator 206 is used at the end of the reference arm 202 to eliminate non-PM birefringence effects in the reference arm 202. The 22.5° faraday rotator 200 splits the light from the reference arm 202 equally between the two polarization states. A Faraday rotator 200 which rotates the polarization state by an angle other than 22.5° can also be used, resulting in differing amounts of light from the reference arm being coupled into each of the polarization states. Differing light levels from the reference arm on the two detectors makes it more difficult to operate both detectors at optimum power levels.

Light returning from the sample arm 212 is split in an arbitrary manner between the detectors 188,190 based on its polarization state. Once again, the envelope of the heterodyne signals from the detectors 188,190 are summed to determine the amount of light returning from the sample arm 212. An advantage of this system is that a large fraction of the initial light can be coupled through the coupler 184 and back, through the use of a non 50/50 coupler. For example, a 90/10 coupler could be used to transfer 90% of the light from the source arm 180 to the sample arm 212, and 90% of the light from the sample arm 212 back to the source arm 180. In addition, one could use a 1×2 coupler instead of the 2×2 coupler, as the second input is no longer needed. Alternatively, a bulk optic beamsplitter can be used in place of the coupler 184, eliminating the use of optical fiber 204.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

What is claimed is:

1. An optical coherence domain reflectometry (OCDR) system, comprising:

a source arm that introduces polarized light into a sample arm and a reference arm;

a sample arm having a path length and comprising optical fiber that transmits the polarized light to a sample and collects light reflected from the sample, wherein the optical fiber comprises at least a section of non-polarization maintaining (non-PM) fiber, a reference arm having a path length and comprising optical fiber that transmits the polarized light to a reference mirror and collects light reflected from the mirror, wherein the optical fiber comprises at least a section of non-polarization maintaining non-PM fiber, an optical rotator element situated in the reference arm between the non-PM fiber and the reference mirror that rotates the polarization of the light; and a detector system that collects the reflected light from the sample arm and the reference arm and measures the power of the light collected from the sample arm as a function of a propagation distance, independent of the polarization state of the light collected from the sample arm, and wherein the reflected light from the reference arm enters the detector system having a defined polarization state that is independent of changes in birefringence in the non-PM fiber in the reference arm.

2. An OCDR system as recited in claim 1, further comprising a piezoelectric transducer to vary the path length of the reference arm with respect to the path length of the sample arm.

3. An OCDR system as recited in claim 1, wherein the section of non-PM optical fiber in the reference arm is substantially equal in length to the section of non-PM optical fiber in the sample arm.

4. An OCDR system as recited in claim 1, wherein the sample arm further comprises means for transversely scanning light across the sample, and wherein the detector arm further comprises means for generating a cross-sectional image of the sample.

5. An OCDR system as recited in claim 1, wherein the detector system comprises a plurality of detectors and a first optical element positioned before at least one of the detectors that splits the collected light into two orthogonal polarization modes, each polarization mode being detected by at least one of the detectors.

6. An OCDR system as recited in claim 5, wherein the first optical element positioned before the detectors comprises a polarization beam splitter that splits the light from the reference arm into the two polarization modes.

7. An OCDR system as recited in claim 5, wherein the first optical element positioned before the detectors splits the light from the reference arm equally into the two polarization modes.

8. An OCDR system as recited in claim 5, wherein the optical rotator element rotates the polarization of the light by about 45° before reflecting off the reference mirror and by about 90° upon double passing of the optical rotator element.

9. An OCDR system as recited in claim 8, wherein the optical fiber in the sample arm and reference arm consists essentially of non-PM optical fiber.

10. An OCDR system as recited in claim 9, further comprising a bulk optic beamsplitter positioned between the source arm and the sample arm and between the source arm and the reference arm.

11. An OCDR system as recited in claim 9, further comprising a fiber optic non-PM coupler positioned between the source arm and the sample arm and between the source arm and the reference arm.

12. An OCDR system as recited in claim 11, wherein the detector system is incorporated into the source arm.

13. An OCDR system as recited in claim 12, wherein the detector system further comprises a second optical element, wherein the first optical element and the second optical element are each positioned before at least one of the detectors, wherein the first optical element splits the collected light into two orthogonal polarization modes and directs at least one mode to at least one detector, and wherein the second optical element directs the remaining collected light to at least one detector, and wherein the detector system further comprises a third optical element that rotates the polarization of the light by about 45° before entering the coupler and by about 90° upon double passing of the third optical element, and wherein the third optical element is positioned between the first and second optical elements.

14. An OCDR system as recited in claim 13, further comprising a half wave plate positioned between the first optical element and the second optical element.

15. An OCDR system as recited in claim 13, further comprising a faraday rotator positioned between the first and second optical elements and the coupler, wherein the rotator rotates the polarization of the light by about 22.5° before entering the coupler and by about 45° upon double passing of the rotator.

16. An OCDR system as recited in claim 13, wherein the optical fiber in the source arm and detector system consists essentially of non-PM fiber that transmits light to and from the coupler.

17. An OCDR system as recited in claim 13, wherein the coupler does not split the light equally between the sample arm and the reference arm.

18. An OCDR system as recited in claim 17, wherein the coupler sends more than 50% of the light from the source arm to the sample arm.

19. An OCDR system as recited in claim 8, further comprising a bulk optic beamsplitter that splits the polarized light from the source arm between the reference arm and the sample arm, and returns the light from the reference arm and sample arm to the source arm and detector system, wherein the beamsplitter is positioned between the source arm and the sample arm and between the source arm and the reference arm, and wherein the detector system is incorporated into the source arm, and wherein the detector system further comprises a second optical element, wherein the first optical element and the second optical element are each positioned before at least one of the detectors so as to split the collected light into two orthogonal polarization modes, each polarization mode being detected by at least one of the detectors, and wherein the detector system further comprises a third optical element that rotates the polarization of the light by about 45° before entering the beamsplitter and by about 90° upon double passing of the third optical element, and wherein the third optical element is positioned between the first and second optical elements.

20. An OCDR system as recited in claim 5, further comprising a second optical element that modifies the polarization of the light passing from the source to the reference arm mirror and then to the detector system.

21. An OCDR system as recited in claim 20, wherein the second optical element rotates the polarization state of the light by about 45° upon double passing of the second optical element.

22. An OCDR system as recited in claim 20, wherein the second optical element comprises a faraday rotator or a wave plate.

23. An OCDR system as recited in claim 20, wherein the second optical element is situated in the reference arm such that the light from the source arm entering the reference arm passes through the second optical element before the non-PM fiber in the reference arm.

24. An OCDR system as recited in claim 23, wherein the reference arm further comprises a section of PM fiber, and wherein the second optical element is positioned between the PM fiber and the non-PM fiber in the reference arm.

25. An OCDR system as recited in claim 20, further comprising a fiber optic PM coupler positioned between the source arm and the sample arm and between the source arm and the reference arm.

26. An OCDR system as recited in claim 25, wherein the sample arm comprises a section of PM optical fiber and the reference arm comprises a section of PM optical fiber, and the sections are substantially equal in length.

27. An OCDR system as recited in claim 1, wherein the optical rotator element comprises a faraday rotator.

28. An OCDR system as recited in claim 1, wherein at least a portion of the non-PM optical fiber in the reference arm is a replaceable section.

29. An OCDR system as recited in claim 1, wherein at least a portion of the non-PM optical fiber in the sample arm is a replaceable section.

30. An OCDR system as recited in claim 1, wherein at least a portion of the non-PM optical fiber in the sample arm is a replaceable section, and wherein at least a portion of the non-PM optical fiber in the reference arm is a replaceable section, and the sections are substantially equal in length.

31. An OCDR system as recited in claim 1, wherein the path length of the reference arm and the path length of the sample arm are substantially equal.

32. An OCDR system as recited in claim 1, wherein the sample arm further comprises a device at the distal end of the non-PM optical fiber.

33. An OCDR system as recited in claim 32, wherein the device is selected from the group consisting of lenses, prisms, mirrors, and wave plates.

34. An OCDR system as recited in claim 1, wherein a distal section of the non-PM optical fiber in the sample arm is incorporated into a device selected from the group consisting of guidewires, catheters, handpieces, and probes.

35. An OCDR system as recited in claim 1, wherein the sample arm further comprises a plurality of non-PM optical fibers, each fiber having a distal end and a proximal end, and an optical switch or multiplexer connected to the proximal ends of the fibers to sequentially switch to each of the fibers.

36. A method for imaging at least a single point in a sample using an optical coherence domain reflectometry (OCDR) system, comprising:

introducing polarized light into a sample arm and a reference arm;

transmitting the polarized light to the sample through at least a section of non-polarization maintaining (non-PM) optical fiber;

collecting light reflected from the sample and from the reference mirror;

splitting the collected light into two polarization modes, wherein each mode is detected by at least one detector;

detecting the collected light using a plurality of detectors, and wherein the reflected light from the reference arm enters the detector system having a defined polarization state that is independent of changes in birefringence in the non-PM fiber in the reference arm; and processing the detected light to generate a measurement of the sample at a point.

37. A method as recited in claim 36, further comprising transversely scanning light across the sample and generating a cross-sectional image of the sample.

38. A method as recited in claim 36, further comprising rotating the polarization of the light by about 45° using the optical rotator element before reflecting off the reference mirror and by about 90° upon double passing of the rotator element.

39. A method as recited in claim 38, further comprising bending the non-PM fiber in the reference arm such that the polarized light entering the detector system is split equally between the two polarization modes.

40. A method as recited in claim 36, further comprising modifying the polarization of the light passing from the source to the reference arm mirror and then to the detector system by about 22.5° per pass using a second optical element.

41. A method as recited in claim 40, further comprising passing the light from the source arm to the reference arm mirror through the second optical element before the non-PM fiber in the reference arm.

42. A method as recited in claim 40, further comprising passing the light from the source arm to the reference arm mirror through a section of PM fiber, the second optical element, the non-PM fiber in the reference arm, and the optical rotator element.

43. A method as recited in claim 36, further comprising passing the light in the sample arm and in the reference arm through optical fiber consisting essentially of non-PM optical fiber.

44. A method as recited in claim 43, further comprising passing the collected light to the detectors through at least two optical elements, wherein the optical elements are each positioned before at least one of the detectors so as to split the collected light into the two polarization modes.

45. A method as recited in claim 44, further comprising rotating the polarization of the light passing from the source to the reference arm mirror by about 45° per pass between the optical elements positioned before the detectors using a third optical element.

46. A method as recited in claim 45, further comprising rotating the polarization of the light passing from the source to the reference arm mirror by about 22.5° per pass after the optical elements positioned before the detectors.

47. A method as recited in claim 36, further comprising splitting the light unequally between the sample arm and the reference arm.

48. A method as recited in claim 36, further comprising transmitting the light to the sample through a device at the distal end of the non-PM optical fiber in the sample arm.

* * * * *